US012617925B2

(12) United States Patent
Kim et al.

(10) Patent No.: US 12,617,925 B2
(45) Date of Patent: May 5, 2026

(54) METHOD FOR PRODUCING BIS(2-HYDROXYETHYL)TEREPHTHALATE BY USING RECYCLED ETHYLENE GLYCOL

(71) Applicant: SK CHEMICALS CO., LTD., Seongnam-si (KR)

(72) Inventors: Ji-Hun Kim, Seongnam-si (KR); Joong Ki Lee, Seongnam-si (KR); Kwang-Woo Park, Seongnam-si (KR); Seong-Ki Lee, Seongnam-si (KR); Yuntae Jin, Seongnam-si (KR)

(73) Assignee: SK CHEMICALS CO., LTD., Seongnam-si (KR)

( * ) Notice: Subject to any disclaimer, the term of this patent is extended or adjusted under 35 U.S.C. 154(b) by 0 days.

(21) Appl. No.: 18/696,639

(22) PCT Filed: Sep. 4, 2023

(86) PCT No.: PCT/KR2023/013141
§ 371 (c)(1),
(2) Date: Mar. 28, 2024

(87) PCT Pub. No.: WO2024/053955
PCT Pub. Date: Mar. 14, 2024

(65) Prior Publication Data
US 2024/0392098 A1 Nov. 28, 2024

(30) Foreign Application Priority Data
Sep. 5, 2022 (KR) ........................ 10-2022-0112190

(51) Int. Cl.
*C08J 11/24* (2006.01)
*C07C 29/80* (2006.01)
(Continued)

(52) U.S. Cl.
CPC ............... *C08J 11/24* (2013.01); *C07C 29/80* (2013.01); *C07C 67/03* (2013.01); *C07C 69/82* (2013.01); *C08J 2367/06* (2013.01)

(58) Field of Classification Search
CPC ....... C08J 11/24; C08J 2367/03; C07C 29/80; C07C 69/82; C07C 67/54
See application file for complete search history.

(56) References Cited

U.S. PATENT DOCUMENTS

2019/0161595 A1* 5/2019 Charra .................... C07C 67/54

FOREIGN PATENT DOCUMENTS

EP 4 375 268 A1 5/2024
JP 2000-169623 A 6/2000
(Continued)

OTHER PUBLICATIONS

JP2003055300 A, Inada Shuji et al., Method for producing bis-beta-hydroxyethyl terephthalate, English translation, 14 pages (Year: 2003).*
(Continued)

*Primary Examiner* — Yate' K Cutliff
(74) *Attorney, Agent, or Firm* — Sughrue Mion, PLLC

(57) ABSTRACT

A method for producing bis(2-hydroxyethyl)terephthalate is disclosed. The method includes recovering and reusing ethylene glycol with an acetate removed, after the glycolysis of a waste polyester. According to the method, an acetate is not concentrated even though ethylene glycol is reused in a continuous process, leading to bis(2-hydroxyethyl)terephthalate with excellent purity and quality.

8 Claims, 1 Drawing Sheet

(51) Int. Cl.
*C07C 67/03* (2006.01)
*C07C 69/82* (2006.01)

(56) References Cited

FOREIGN PATENT DOCUMENTS

| | | | | | |
|---|---|---|---|---|---|
| JP | 200016923 | A | * | 6/2000 | ............. C08J 11/24 |
| JP | 2001048835 | A | * | 2/2001 | ............. C07C 67/03 |
| JP | 2003055300 | A | * | 2/2003 | ............. C08J 11/24 |
| JP | 2005-330444 | A | | 12/2005 | |
| JP | 2008-088096 | A | | 4/2008 | |
| KR | 1998-0058164 | A | | 9/1998 | |
| KR | 10-2021-0067555 | A | | 6/2021 | |
| KR | 10-2022-0068991 | A | | 5/2022 | |
| WO | 2020/156966 | A1 | | 8/2020 | |
| WO | 2021/028695 | A1 | | 2/2021 | |
| WO | WO-2021167556 | A1 | * | 8/2021 | ............. C08J 11/16 |
| WO | 2022/171874 | A1 | | 8/2022 | |

OTHER PUBLICATIONS

JP2000169623 A, Inada Shuji et al., Chemical recycle of polyethylene terephthalate waste, English translation, 12 pages (Year: 2000).*

JP2002048835 A, Inada Shuji, Purification of crude bis-beta-hydroxethyl terephthalate and the resultant purified bis-beta-hydroxyethyl terephthalate, English translation, 9 pages (Year: 2001).*

Damayanti, Strategic possibility routes of recycled PET, Polymers, 13, 475, 37 pages (Year: 2001).*

International Search Report for PCT/KR2023/013141, dated Nov. 30, 2023.

European Patent Office, Communication issued Oct. 31, 2025 in copending Application No. EP 23 86 1686.

* cited by examiner

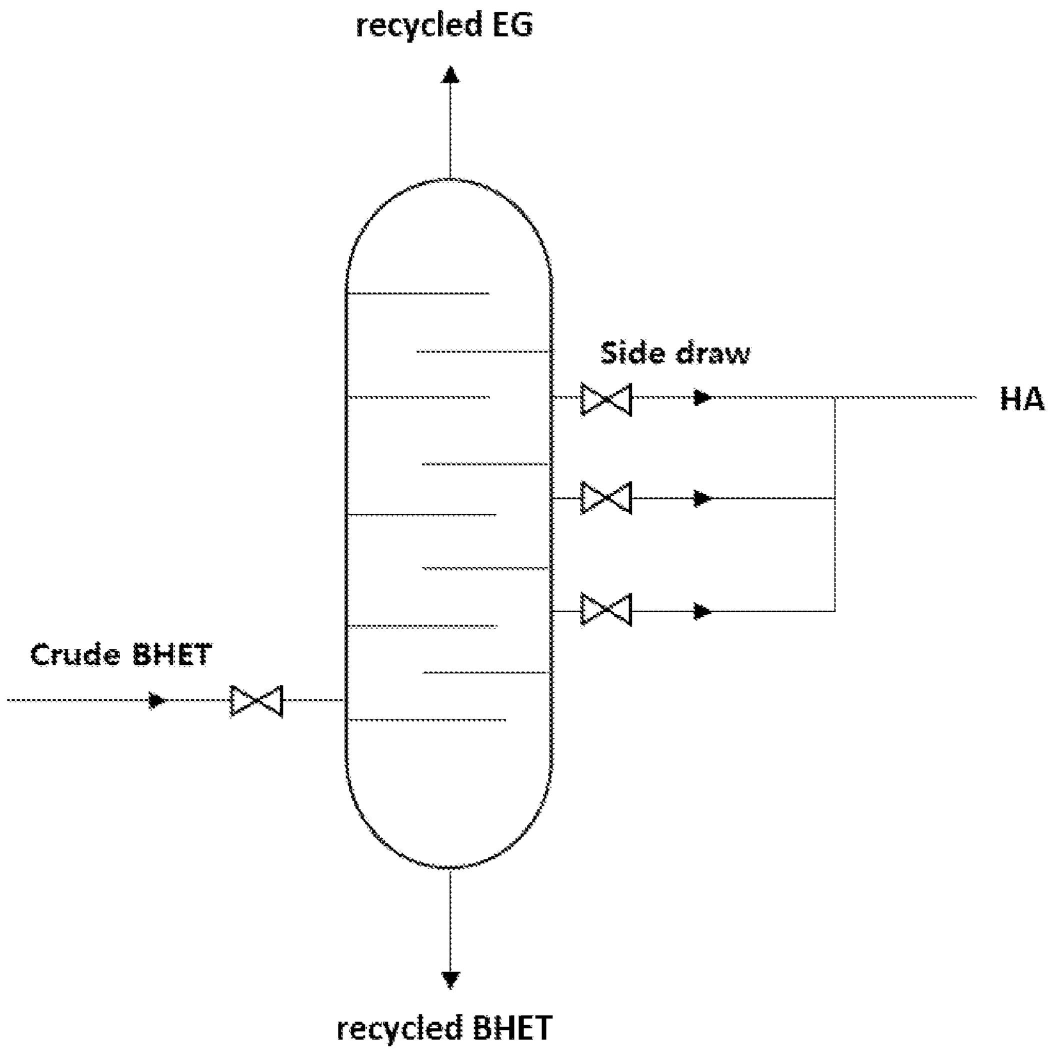
recycled EG
Side draw
HA
Crude BHET
recycled BHET

METHOD FOR PRODUCING BIS(2-HYDROXYETHYL)TEREPHTHALATE BY USING RECYCLED ETHYLENE GLYCOL

CROSS REFERENCE TO RELATED APPLICATIONS

This application is a National Stage of International Application No. PCI/KR2023/013141 filed Sep. 4, 2023, claiming priority based on Korean Patent Application No. 10-2022-0112190 filed Sep. 5, 2022.

TECHNICAL FIELD

The present invention relates to a process for preparing bis(2-hydroxyethyl) terephthalate using recycled ethylene glycol in the depolymerization process of waste polyester.

BACKGROUND ART

Polyester is widely used as a material for beverage-filling containers, packaging films, audio and video films, and the like by virtue of its excellent mechanical strength, thermal resistance, transparency, and gas barrier properties. In addition, polyester is widely produced worldwide as an industrial material such as medical fibers and tire cords. In particular, polyester sheets or plates have good transparency and excellent mechanical strength, so that they are widely used as raw materials for cases, boxes, partitions, shelves, panels, packaging materials, building materials, interior and exterior materials, and the like.

As a result, waste of plastics such as polyester is generated globally at an unmanageable level every year. Recently, countries around the world have prepared regulations and plans for recycling waste plastic resources, including waste polyester. Although physical or chemical methods are used as methods of recycling waste polyester, physical recycling methods cannot guarantee purity and, thus, are not widely used.

Meanwhile, in chemical recycling methods, the ester bond of waste polyester is severed to depolymerize it. Reactions such as glycolysis, hydrolysis, methanolysis, and aminolysis are used. Glycolysis among them is to decompose waste polyester by adding a glycol such as ethylene glycol or diethylene glycol at high temperatures. A reaction product comprising mainly bis(2-hydroxyethyl) terephthalate (BHET) is obtained. The bis(2-hydroxyethyl) terephthalate contained in the reaction product may be used as a raw material for preparing unsaturated polyester or ester polyol after the crystallization or purification thereof.

In order to use bis(2-hydroxyethyl) terephthalate as the above raw material, it is necessary to increase the purity of bis(2-hydroxyethyl) terephthalate by minimizing the formation of by-products such as diethylene glycol esters (DEG esters) during the depolymerization process. To this end, a method of performing depolymerization by designing continuous stirred tank reactors (CSTRs) in multiple stages is currently adopted.

PRIOR ART DOCUMENT (Patent Document 1) Korean Laid-open Patent Publication No. 2022-0068991

DISCLOSURE OF INVENTION

Technical Problem

An excessive amount of ethylene glycol is added to a glycolysis reaction for the production of bis(2-hydroxyethyl) terephthalate. Thus, it is common to recover and reuse it to increase cost efficiency, and it is required to manage the purity of ethylene glycol circulated in this process.

However, the content of by-products in ethylene glycol increases during this continuous process. These by-products are converted to esters through a glycolysis reaction, causing a problem of deteriorating the quality of a final bis(2-hydroxyethyl) terephthalate.

The present inventors paid attention to the accumulation of acetate-based compounds originating from the catalysts in ethylene glycol reused in a continuous glycolysis process and have been able to solve this problem by removing them during the recovery process of ethylene glycol.

In particular, the acetate-based compounds accumulated in the above process have similar boiling points to that of ethylene glycol; thus, it is not easy to separate them through a distillation column. However, it has been possible to do so by side draw purging at a specific fraction from the stages with the highest concentration of acetate-based compounds in a multi-stage distillation column.

Accordingly, an object of the present invention is to provide a process for preparing bis(2-hydroxyethyl) terephthalate while preventing acetate compounds from being concentrated when ethylene glycol is reused in a continuous glycolysis process and to provide bis(2-hydroxyethyl) terephthalate with excellent purity and quality.

Solution to Problem

According to an aspect of the present invention, there is provided a process for preparing recycled bis(2-hydroxyethyl) terephthalate, which comprises (a) depolymerizing waste polyester by glycolysis to obtain a crude bis(2-hydroxyethyl) terephthalate solution; (b) distilling the crude bis(2-hydroxyethyl) terephthalate solution to separate a distillate comprising ethylene glycol; (c) removing an acetate-based compound from the distillate to recover the ethylene glycol; and (d) reusing the recovered ethylene glycol for the glycolysis.

In a specific embodiment, the glycolysis in step (a) comprises a reaction of waste polyester and ethylene glycol in the presence of an acetate-based catalyst; the separation of the distillate in step (b) is carried out using a distillation column at a pressure of 0.1 Torr to 300 Torr and a temperature of 70° C. to 170° C.; the removal of the acetate-based compound in step (c) is carried out by side draw purging at a specific fraction in the distillation column; and, in step (d), the ethylene glycol recovered as a result is reused for the glycolysis in step (a), which may be carried out repeatedly in a continuous process.

According to another aspect of the present invention, there is provided recycled bis(2-hydroxyethyl) terephthalate, which is obtained by the depolymerization of waste polyester, wherein the peak area fraction of bis(2-hydroxyethyl) terephthalate is 97% or more, and the peak area fraction of acetate-based ester compounds is 1% or less, when measured by high-performance liquid chromatography (HPLC).

Advantageous Effects of Invention

In the process for preparing bis(2-hydroxyethyl) terephthalate of the present invention, ethylene glycol from which acetate-based compounds have been removed after the glycolysis of waste polyester is recovered and reused. Thus, even if ethylene glycol is reused in a continuous process, acetate-based compounds are not concentrated, and bis(2-hydroxyethyl) terephthalate with excellent purity and quality can be obtained.

According to a specific embodiment, in the process of separating low-boiling point compounds comprising ethylene glycol by feeding a crude product solution of glycolysis to a multi-stage distillation column, acetate-based compounds are removed through side draw purging, and acetate-based ester compounds can be prevented from being concentrated in the finally obtained bis(2-hydroxyethyl) terephthalate.

The recycled bis(2-hydroxyethyl) terephthalate obtained as a result has excellent purity and color and has high crystallinity; thus, it can be used to prepare environmentally friendly polyester products with a high melting point.

BRIEF DESCRIPTION OF DRAWINGS

The FIGURE illustrates a distillation column used in the process for preparing bis(2-hydroxyethyl) terephthalate according to an embodiment of the present invention.

BEST MODE FOR CARRYING OUT THE INVENTION

In this specification, terms referring to the respective components are used to distinguish them from each other and are not intended to limit the scope of the embodiment. In addition, in the present specification, a singular expression is interpreted to cover a plural number as well unless otherwise specified in the context.

In the present specification, the terms first, second, and the like are used to describe various components. But the components should not be limited by the terms. The terms are used for the purpose of distinguishing one element from another.

In the present specification, the term "comprising" is intended to specify a particular characteristic, region, step, process, element, and/or component. It does not exclude the presence or addition of any other characteristic, region, step, process, element and/or component, unless specifically stated to the contrary.

The molecular weight of a compound or polymer described in the present specification, for example, a number average molecular weight or a weight average molecular weight, is a relative mass based on carbon-12 as is well known. Although its unit is not described, it may be understood as a molar mass (g/mole) of the same numerical value, if necessary.

According to an aspect of the present invention, there is provided a process for preparing bis(2-hydroxyethyl) terephthalate in which waste polyester is depolymerized, and ethylene glycol from which acetate-based compounds have been removed is recovered and reused.

The process for preparing bis(2-hydroxyethyl) terephthalate according to an embodiment comprises (a) depolymerizing waste polyester by glycolysis to obtain a crude bis(2-hydroxyethyl) terephthalate solution; (b) distilling the crude bis(2-hydroxyethyl) terephthalate solution to separate a distillate comprising ethylene glycol; (c) removing an acetate-based compound from the distillate to recover the ethylene glycol; and (d) reusing the recovered ethylene glycol for the glycolysis.

According to the above process, ethylene glycol from which acetate-based compounds have been removed after the glycolysis of waste polyester is recovered and reused. Thus, even if ethylene glycol is reused in a continuous process, acetate-based compounds are not concentrated, and bis(2-hydroxyethyl) terephthalate with excellent purity and quality can be obtained. According to a specific embodiment, in the process of separating low-boiling point compounds comprising ethylene glycol by feeding a crude product solution of glycolysis to a multi-stage distillation column, acetate-based compounds are removed through side draw purging, and acetate-based ester compounds can be prevented from being concentrated in the finally obtained bis(2-hydroxyethyl) terephthalate.

Hereinafter, each step of the process for preparing bis(2-hydroxyethyl) terephthalate will be described in detail.

Depolymerization of Waste Polyester

First, waste polyester is depolymerized by glycolysis to obtain a crude bis(2-hydroxyethyl) terephthalate solution (step (a)).

The waste polyester raw material may be obtained from a polyester material product discarded after use. Specifically, the waste polyester may be obtained by pretreating waste products such as beverage bottles, fabrics, films, cases, boxes, partitions, shelves, protective panels, packaging materials, building materials, and interior and exterior materials, which comprise various polyester materials (e.g., polyethylene terephthalate (PET) material) discarded after having been used by consumers.

The pretreatment may be carried out by removing other plastics, metals, and foreign substances mixed in the waste, washing it, and then crushing it through a crusher. As a result of the pretreatment, the waste polyester raw material may have a flake form. In addition, the waste polyester raw material may have a fine structure like a fiber.

The waste polyester pretreated in this way is then subjected to a depolymerization process. The depolymerization process may comprise, for example, a glycolysis reaction. As is well known, the glycolysis reaction refers to a chemical reaction in which a polymer chain or the like is severed by a glycol such as ethylene glycol. The total weight of the glycol added may be 1, 2, or 3 times the weight of the waste polyester resin or more and may be 7, 5, or 4 times or less. For example, the weight of the glycol added may be 1 to 7 times, specifically, 2 to 5 times, more specifically, 3 to 4 times, relative to the weight of the waste polyester resin.

A catalyst may be used in the glycolysis reaction. The catalyst may be a metal catalyst, for example, a metal salt catalyst or a metallic organic catalyst. Specifically, the catalyst may be an acetate, carbonate, oxide, or hydroxide of a metal, and the metal may be an alkali metal, an alkali earth metal, or a transition metal. As a specific example, the catalyst comprises a metal acetate, or an anhydride or a hydride thereof. More specifically, it may be at least one selected from the group consisting of zinc acetate, sodium acetate, cobalt acetate, and manganese acetate, or in the form of a hydrate or anhydride thereof. In addition, the weight of the catalyst added may be 0.01 part by weight or more, 0.1 part by weight or more, 0.2 part by weight or more, or 0.3 part by weight or more, and may be 5 parts by weight or less, 1 part by weight or less, 0.7 part by weight or less, 0.5 part by weight or less, or 0.4 part by weight or less, relative to 100 parts by weight of the waste polyester resin. For example, the weight of the catalyst added may be 0.1 part by weight to 1 part by weight, specifically, 0.2 part by weight to 0.7 part by weight, relative to 100 parts by weight of the waste polyester resin. More specifically, the catalyst may be used in an amount of 0.2 part by weight to 0.4 part by weight relative to 100 parts by weight of the waste polyester.

As a specific example, the glycolysis in step (a) may comprise a reaction of waste polyester and ethylene glycol in the presence of an acetate-based catalyst.

The depolymerization may comprise, for example, a multi-stage depolymerization reaction at low temperatures. As a specific example, the depolymerization may comprise subjecting waste polyester to depolymerization through a first glycolysis reaction at a high temperature (180 to 200° C.); and subjecting the product to depolymerization at a low temperature (150 to 170° C.) through a second glycolysis reaction.

The depolymerization in step (a) may be carried out in a continuous process. As a specific example, the continuous process comprises (1) feeding a waste polyester raw material to a co-extruder to obtain a co-extrudate; (2) feeding the co-extrudate to an agitated shaft reactor and depolymerizing it to obtain a first reactant; (3) feeding the first reactant to a first continuous reactor and depolymerizing it to obtain a second reactant; and (4) feeding the second reactant to a second continuous reactor and depolymerizing it to obtain a third reactant, wherein ethylene glycol may be added to at least one of steps (1) to (4).

In step (1) of the continuous process, the reduction in molecular weight of the waste polyester raw material is achieved in a physical and/or chemical way through the co-extruder. First, a first glycol-based compound may be continuously fed to the co-extruder. The first glycol-based compound is not particularly limited. Specifically, it may be at least one selected from the group consisting of ethylene glycol (i.e., monoethylene glycol), propylene glycol, and diethylene glycol. The feeding amount of the first glycol-based compound may be 0.01 to 100 parts by weight relative to 100 parts by weight of the waste polyester raw material. Meanwhile, the co-extrusion may be carried out at 170° C. to 290° C. The co-extruder may not be particularly limited as long as it is designed to co-extrude the waste polyester raw material. Specifically, the co-extruder may be a single-screw co-extruder or a multi-screw (e.g., twin-screw) co-extruder conventionally known. For example, the co-extrudate may have a weight average molecular weight of 3,000 to 36,000. As the co-extrudate obtained through step (1) has a relatively low molecular weight as described above, the time to be spent in the depolymerization procedure in steps (2) to (4) can be shortened while the formation of by-products (e.g., DEG and DEG esters) is minimized.

In step (2) of the continuous process, a glycolysis reaction in which polymer chains and the like present in the co-extrudate are severed by the first glycol-based compound can be carried out within a short time. If the first glycol-based compound is not fed to the co-extruder in step (1), the first glycol-based compound may be continuously fed to the agitated shaft reactor. A catalyst may be further added to the agitated shaft reactor to facilitate the depolymerization reaction. The catalyst may be a catalyst comprising a metal acetate, an anhydride thereof, or a hydrate thereof, as exemplified above. The amount of the catalyst fed to the agitated shaft reactor may be 0.01 to 5 parts by weight relative to 100 parts by weight of the waste polyester raw material. Depolymerization of the co-extrudate may be carried out at 180° C. to 210° C. for 20 minutes to 50 minutes. The agitated shaft reactor may not be particularly limited as long as it is designed to mix the co-extrudate, the first glycol-based compound, and the catalyst. Specifically, the agitated shaft reactor may comprise at least one selected from the group consisting of a kneader, a paddle mixer, a plow shear mixer, a screw mixer, and a ribbon blender. More specifically, it may be a kneader or a paddle mixer.

In step (3) of the continuous process, a second glycol-based compound may be continuously fed to a first continuous reactor. As a result, a glycolysis reaction in which polymer chains and the like present in the first reactant are severed by the second glycol-based compound can be carried out. The second glycol-based compound is not particularly limited. Specifically, it may be at least one selected from the group consisting of ethylene glycol (monoethylene glycol), propylene glycol, and diethylene glycol. The amount of the second glycol-based compound fed to the first continuous reactor may be 50 to 340 parts by weight relative to 100 parts by weight of the first reactant. Depolymerization of the first reactant may be carried out at 170° C. to 195° C. for 30 minutes to 50 minutes. The depolymerization of the first reactant may be carried out in the presence of the catalyst continuously fed to the agitated shaft reactor in step (2) or a catalyst directly fed to the first continuous reactor. The catalyst may be a catalyst comprising a metal acetate, an anhydride thereof, or a hydrate thereof, as exemplified above. Meanwhile, the first continuous reactor may not be particularly limited as long as it is a continuous flow tank reactor designed to carry out depolymerization.

In step (4) of the continuous process, a glycolysis reaction in which polymer chains and the like present in the second reactant are severed by the unreacted second glycol-based compound, which is discharged from the first continuous reactor of step (1) and supplied to the second continuous reactor, can be carried out. A third glycol-based compound may be additionally fed to the second continuous reactor in preparation for a decrease in the depolymerization efficiency when the unreacted second glycol-based compound is not supplied to the second continuous reactor to the extent that the depolymerization is sufficiently carried out, or when the purity of the unreacted second glycol-based compound is lowered. The third glycol-based compound is not particularly limited. Specifically, it may be at least one selected from the group consisting of ethylene glycol (monoethylene glycol), propylene glycol, and diethylene glycol. The amount of the third glycol-based compound fed to the second continuous reactor may be 50 to 150 parts by weight relative to 100 parts by weight of the second reactant. Depolymerization of the second reactant may be carried out at 140° C. to 170° C. for 30 minutes to 50 minutes. The depolymerization of the second reactant may be carried out in the presence of the catalyst continuously fed to the agitated shaft reactor in step (2), the catalyst continuously fed to the first continuous reactor, or a catalyst directly fed to the second continuous reactor. The catalyst may be a catalyst comprising a metal acetate, an anhydride thereof, or a hydrate thereof, as exemplified above. Meanwhile, the second continuous reactor may not be particularly limited as long as it is a continuous flow tank reactor designed to carry out depolymerization.

Removal of Acetate-Based Compounds and Recovery of Ethylene Glycol Through Distillation The crude bis(2-hydroxyethyl) terephthalate solution obtained above is distilled to separate a low-boiling point distillate comprising ethylene glycol (step (b)).

The distillation in step (b) may be carried out by, for example, vacuum distillation. A distillation column may be used for this purpose.

The FIGURE illustrates a distillation column used in the process for preparing bis(2-hydroxyethyl) terephthalate according to an embodiment of the present invention. Referring to the FIGURE, the distillation column may be composed of multiple stages, for example, 3 stages or more, 5 stages or more, 6 stages or more, or 7 stages or more, and may be composed of 20 stages or less, 15 stages or less, or 10 stages or more. As a specific example, it may be composed of 7 to 15 stages.

The temperature for separating the distillate in step (b) may be, for example, 60° C. or higher, 70° C. or higher, 80° C. or higher, 90° C. or higher, or 100° C. or higher, and may be 200° C. or lower, 180° C. or lower, 170° C. or lower, 150° C. or lower, or 130° C. or lower. In addition, the pressure for separating the distillate may be, for example, 500 Torr or less, 400 Torr or less, 300 Torr or less, or 270 Torr or less, and may be 0.1 Torr or more, 1 Torr or more, 10 Torr or more, 100 Torr or more, or 200 Torr or more. As a specific example, the separation of the distillate in step (b) may be carried out using a distillation column at a pressure of 0.1 Torr to 300 Torr and a temperature of 70° C. to 170° C.

The acetate-based compound in step (c) may have one glycol group in the molecule and may not contain an aromatic group in the molecule.

Specifically, the acetate-based compound in step (c) may comprise 2-hydroxyethyl acetate.

As shown in the following Reaction Scheme 1, acetic acid (AA) derived from metal acetate, which is mainly used as a catalyst, may react with ethylene glycol (EG) to produce an acetate-based compound such as 2-hydroxyethyl acetate (HA) and water ($H_2O$).

[Reaction Scheme 1]

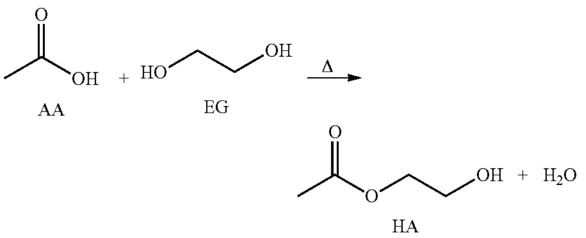

Thereafter, the acetate-based compound is removed from the distillate to recover ethylene glycol (step (c)).

The removal of the acetate-based compound in step (c) may be carried out by side draw purging in the distillation column.

Referring to the FIGURE, in the distillate comprising low-boiling compounds primarily separated from the crude BHET solution, specifically ethylene glycol (EG) and other trace compounds, acetate-based compounds (HA and the like) may be present at a high concentration in certain stages, while it passes through several stages in the distillation column, from which the acetate-based compounds such as 2-hydroxyethyl acetate (HA) may be discharged out of the system through side draw purging. As a result, as ethylene glycol (EG) from which acetate-based compounds have been removed is recovered, accumulation of acetate-based compounds during circulation of ethylene glycol can be effectively prevented. For this purpose, the distillation column may be equipped with a pipe for discharging acetate-based compounds out of the system at a specific stage and a nozzle for controlling the discharge amount (fraction).

As a specific example, the interior of the distillation column may be divided into a total of 5 to 20 stages, and side draw purging may be performed between the 2nd to 10th stages from the top. As another specific example, the interior of the distillation column may be divided into a total of 10 to 15 stages, and side draw purging may be performed between the 2nd to 8th stages from the top. In addition, the internal temperature of the stage where the side draw purging is performed may be 70° C. to 170° C., more specifically 90° C. to 150° C.

The fraction of the side draw purging may be, for example, 3% by weight or less, 1% by weight or less, 0.7% by weight or less, 0.5% by weight or less, or 0.3% by weight or less, and may be 0.001% by weight or more, 0.01% by weight or more, 0.05% by weight or more, 0.1% by weight or more, 0.2% by weight or more, 0.3% by weight or more, or 0.4% by weight or more, based on the total weight of the crude bis(2-hydroxyethyl) terephthalate solution. As a specific example, the side draw purging may be performed at a fraction of 0.05% by weight to 1% by weight based on the total weight of the crude bis(2-hydroxyethyl) terephthalate solution.

In general, ethylene glycol recovered from the depolymerization result of waste polyester through glycolysis, that is, recycled ethylene glycol (REG) may contain reagents or solvents used in various chemical steps or by-products formed by side reactions with them. Thus, such recycled ethylene glycol needs to be understood separately from virgin ethylene glycol. For this reason, recycled ethylene glycol can be viewed as a kind of composition comprising two or more components, i.e., an ethylene glycol composition. Recycled ethylene glycol recovered by a common depolymerization method contains organic and inorganic impurities in addition to ethylene glycol as the main component; thus, its purity may not be high.

However, ethylene glycol recovered in step (d) of the process according to the present invention may have high purity and a particularly low content of acetate-based compounds. For example, the recovered ethylene glycol, that is, recycled ethylene glycol, may have a purity of 95% or more, 97% or more, 98% or more, 99% or more, or 99.5% or more. The purity of recycled ethylene glycol or the content of specific components may be obtained by quantifying the peak area fraction obtained by gas chromatography (GC) analysis using a calibration curve of a standard substance.

When analyzed by gas chromatography (GC), ethylene glycol recovered in step (d), that is, recycled ethylene glycol, may have a content of acetate-based compounds of, for example, 3% by weight or less or 2% by weight or less. As a specific example, the content of acetate-based compounds in the recycled ethylene glycol may be 1% by weight or less. More specifically, the content of acetate-based compounds may be 0.7% by weight, 0.5% by weight, 0.3% by weight, or 0.1% by weight.

For example, the content of monoethylene glycol (MEG) in the recycled ethylene glycol recovered in step (d) may be 95% by weight or more, 97% by weight or more, 98% by weight or more, 99% by weight or more, or 99.5% by weight or more. In addition, the content of diethylene glycol (DEG) in the recycled ethylene glycol may be, for example, 1% by weight or less, 0.5% by weight or less, or 0.3% by weight or less. In addition, the content of triethylene glycol (TEG) in the recycled ethylene glycol may be, for example, 0.3% by weight or less, 0.1% by weight or less, or 0.05% by weight or less.

The ethylene glycol recovered in this way, that is, recycled ethylene glycol, may be reused for the glycolysis in step (a) (step (d)). The number of reuses of ethylene glycol may be, for example, 2 times or more, 3 times or more, 4 times or more, or 5 times or more, and may be 100 times or fewer, 50 times or fewer, 30 times or fewer, 20 times or fewer, or 10 times or fewer. As a specific example, it may be 2 to 20 times or 3 to 10 times.

Even though ethylene glycol that is recycled by recovering ethylene glycol present in excess in the glycolysis reaction product is circulated in the continuous reaction to be repeatedly used several times, impurities, especially acetate-based compounds, are prevented from being accumulated, whereby purity and quality can be maintained.

Meanwhile, the recycled bis(2-hydroxyethyl) terephthalate obtained by first separation of the distillate comprising ethylene glycol from the crude bis(2-hydroxyethyl) terephthalate solution may undergo additional purification.

As a specific example, the recycled bis(2-hydroxyethyl) terephthalate may be prepared by further carrying out at least one of thin-film distillation under reduced pressure; and dissolution in water and adsorption-crystallization.

The thin-film distillation is a distillation method that makes a mixture to be separated into a thin film for increasing its surface area in contact with a heat source. Specifically, a mixture fed to the evaporator of the thin film evaporator forms a thin film on the inner wall of the thin film evaporator by the wiper rotor. Then, distillation is carried out under appropriate temperature conditions by heating. In addition, a condenser for recovering the evaporated material may be provided inside the thin film evaporator. The thin film evaporation may be carried out by short path evaporation. Since such a short path and thin film evaporation has a short residence time and enables vacuum distillation using a high vacuum, it is possible to separate high-boiling or high-molecular-weight materials that are hardly separated by other distillation methods while minimizing the change of the reactants by heat. In addition, if the pressure inside a thin film evaporator is lowered, there is an advantage in that the vapor pressure of a material is reduced, which allows evaporation to take place at a lower temperature than its original boiling point. As a specific example, the reactant in the previous step is fed to a short path and thin film evaporator, and a wiper for forming a thin film is rotated at 300 rpm or more. As a result, a vaporized material and a non-vaporized material can be separated from each other. The internal thin film temperature of the upper thin film evaporation apparatus during the thin film evaporation may be, for example, 150° C. to 250° C., 190° C. to 250° C., or 180° C. to 220° C. In addition, the internal pressure of the upper thin film evaporation apparatus during the thin film evaporation may be, for example, 0.005 Torr to 5.0 Torr, 0.05 Torr to 5.0 Torr, 0.05 Torr to 1.5 Torr, or 0.05 Torr to 1 Torr.

The adsorption-crystallization may be carried out by, for example, adding an adsorbent using water as a solvent, filtering, and crystallization. Various solvents may be used for the adsorption-crystallization, but a solvent capable of dissolving bis(2-hydroxyethyl) terephthalate is preferably used as a solvent. As a specific example, in order to obtain the final reactant, water as a solvent is added to the recycled bis(2-hydroxyethyl) terephthalate, which is dissolved by heating, and an adsorbent is added thereto, followed by subjecting the solution obtained by filtration to cooling-crystallization and final filtration. As a result, bis(2-hydroxyethyl) terephthalate with high purity can be obtained. Water may be added in an amount of 100 parts by weight to 500 parts by weight, specifically, 200 parts by weight to 400 parts by weight, more specifically, 300 parts by weight to 350 parts by weight, relative to 100 parts by weight of the recycled bis(2-hydroxyethyl) terephthalate. In addition, the dissolution temperature may be 50° C. to 95° C., specifically, 60° C. to 85° C., more specifically, 70° C. to 75° C. The adsorbent added may serve to adsorb and remove other foreign substances. It may be added in an amount of 0.1 part by weight to 3 parts by weight relative to 100 parts by weight of the recycled bis(2-hydroxyethyl) terephthalate. The type and form of the adsorbent are not particularly limited. For example, activated carbon may be used.

Recycled Bis(2-Hydroxyethyl) Terephthalate

The present invention provides recycled bis(2-hydroxyethyl) terephthalate obtained by the process described above.

Bis(2-hydroxyethyl) terephthalate (BHET) is an ester of two ethylene glycols and one terephthalic acid. For example, it is a compound formed as an intermediate in the process of preparing a polyester such as polyethylene terephthalate (PET) through the polymerization of ethylene glycol and terephthalic acid or its ester.

Meanwhile, recycled bis(2-hydroxyethyl) terephthalate obtained by the depolymerization of waste polyester as described above (referred to as recycled BHET) may contain reagents or solvents used in various chemical steps during the depolymerization of waste polyester, or by-products formed by side reactions with them. Thus, recycled bis(2-hydroxyethyl) terephthalate obtained by the depolymerization of waste polyester as described above needs to be understood as distinct from a pure BHET compound. For this reason, recycled BHET can also be viewed as a kind of composition comprising two or more components, i.e., a BHET composition. Such recycled BHET may be used as a raw material for the polymerization of a polyester resin. BHET recycled by a common depolymerization process contains organic and inorganic impurities in addition to BHET as the main component; thus, its purity is not high.

However, recycled bis(2-hydroxyethyl) terephthalate according to the present invention has excellent purity and quality although it is obtained by the depolymerization of waste polyester.

The purity of the recycled BHET may be measured using liquid chromatography or the like. Specifically, the purity of the recycled BHET may be calculated by measuring the fraction (%) of the peak area of BHET out of the total peak area in a spectrum obtained using high-performance liquid chromatography (HPLC).

For example, the purity of the recycled BHET may be 95% or more, 97% or more, 98% or more, 99% or more, or 99.5% or more, and specifically 95% to 100% or 97% to 100%.

The recycled bis(2-hydroxyethyl) terephthalate according to an embodiment may have a peak area fraction of bis(2-hydroxyethyl) terephthalate of 97% or more, more specifically, 98% or more, 99% or more, or 99.5% or more, when measured by high-performance liquid chromatography (HPLC).

Meanwhile, the recycled bis(2-hydroxyethyl) terephthalate may comprise a compound other than BHET, specifically, BHET analogues, BHET oligomers (e.g., dimers, trimers), esters (e.g., DEG esters), and acetate-based compounds (HAET or the like).

As shown in the following Reaction Scheme 2, 2-hydroxyethyl acetate (HA) may be converted to ester compounds such as 2-hydroxyethyl(2-acetoxyethyl) terephthalate (HAET) and ethylene glycol (EG) through a transesterification reaction with bis(2-hydroxyethyl) terephthalate.

[Reaction Scheme 2]

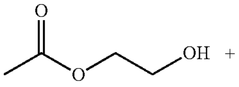

HA

-continued

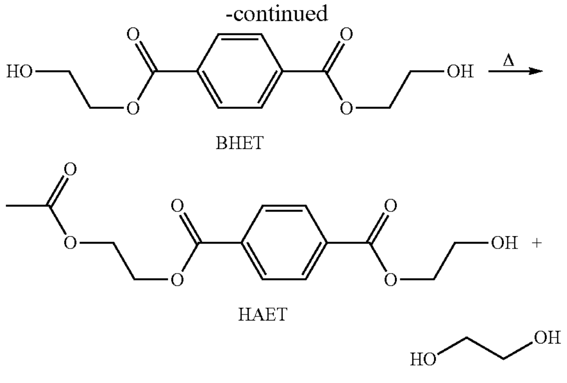

BHET

HAET

EG

The recycled bis(2-hydroxyethyl) terephthalate has a peak area fraction of acetate-based ester compounds of 1% or less when measured by high-performance liquid chromatography (HPLC). Specifically, the recycled bis(2-hydroxyethyl) terephthalate may have a peak area fraction of acetate-based ester compounds of 0.7% or less, 0.5% or less, 0.3% or less, or 0.1% or less, when measured by high-performance liquid chromatography (HPLC). The acetate-based ester compound may be a 2-hydroxyethyl acetate ester compound or a compound containing an aromatic group such as terephthalate. Specifically, it may comprise at least one selected from the group consisting of 2-hydroxyethyl(2-acetoxyethyl) terephthalate (HAET), 2-acetoxyethyl [2-(2-hydroxyethoxy)ethyl] terephthalate, 2-hydroxyethyl [2-[2-(2-hydroxyethoxy)ethoxy]ethyl] terephthalate. As a more specific example, the acetate-based ester compounds may comprise 2-hydroxyethyl(2-acetoxyethyl) terephthalate (HAET).

According to another embodiment, the recycled bis(2-hydroxyethyl) terephthalate may have a peak area fraction of a diethylene glycol (DEG) ester of 2% or less, 1.5% or less, 1% or less, or 0.5% or less, in total when measured by high-performance liquid chromatography (HPLC). As a specific example, the recycled bis(2-hydroxyethyl) terephthalate may have a peak area fraction of a diethylene glycol (DEG) ester of 0.5% or less in total when measured by high-performance liquid chromatography (HPLC). The diethylene glycol ester compound may comprise 2-hydroxyethyl [2-(2-hydroxyethoxy)ethyl] terephthalate and bis [2-(2-hydroxyethoxy)ethyl]benzene-1,4-dicarboxylate.

According to another embodiment, the recycled bis(2-hydroxyethyl) terephthalate may have a peak area fraction of monohydroxyethyl terephthalate (MHET) of 2% or less, 1.5% or less, 1% or less, or 0.5% or less, when measured by high-performance liquid chromatography (HPLC). As a specific example, the recycled bis(2-hydroxyethyl) terephthalate may have a peak area fraction of monohydroxyethyl terephthalate (MHET) of 1% or less when measured by high-performance liquid chromatography (HPLC).

The recycled bis(2-hydroxyethyl) terephthalate has excellent crystallinity, thereby having a high melting point, and has excellent quality such as color.

For example, the recycled bis(2-hydroxyethyl) terephthalate may have a melting point (m.p.) of 107° C. to 117° C., more specifically, 107° C. to 115° C.

In addition, the recycled bis(2-hydroxyethyl) terephthalate may have a yellow index (YID) of 5.0 or less as measured with a colorimeter for a solution of 25% by weight. Specifically, the yellow index may be 5.0 or less, 4.5 or less, 4.0 or less, 3.5 or less, 3.0 or less, 2.5 or less, 2.0 or less, 1.5 or less, or 1.0 or less.

As a specific example, the recycled bis(2-hydroxyethyl) terephthalate may have a melting point of 107° C. to 115° C. and a yellow index (YID) of 5.0 or less when measured for a solution dissolved in dimethylformamide at a concentration of 25% by weight.

MODE FOR THE INVENTION

Hereinafter, a preferred embodiment is presented for the understanding of the present invention. However, the following examples are provided only to help easily understand the present invention, and the scope of the present invention is not limited thereby.

Example 1

Step (1) Preparation of a Crude BHET Solution by Glycolysis

Crushed waste PET and monoethylene glycol (MEG) were fed to a single-screw co-extruder at a feeding rate of 15.5 kg/hr, respectively, and co-extruded (for a reduction in molecular weight) at a temperature of 180° C. and 150 rpm to obtain a co-extrudate. Depolymerization was carried out continuously through a kneader, a first continuous reactor (CSTR-1), and a second continuous reactor (CSTR-2), following the above co-extrusion process. Specifically, the co-extrudate (feeding rate: 31.0 kg/hr) and zinc acetate anhydride (feeding rate: 0.065 kg/hr) as a catalyst were fed to a kneader, and a first depolymerization reaction was carried out at 195° C. for 35 minutes to obtain a first reactant. The first reactant thus obtained and additional monoethylene glycol (MEG) (feeding rate: 15.5 kg/hr) were fed to a first continuous reactor (CSTR-1), and a second depolymerization reaction was carried out at 190° C. for 40 minutes to obtain a second reactant. The second reactant thus obtained and additional monoethylene glycol (MEG) (feeding rate: 31.0 kg/hr) were fed to a second continuous reactor (CSTR-2), and a third depolymerization reaction was carried out at 150° C. for 40 minutes to obtain a third reactant, i.e., a crude bis(2-hydroxyethyl) terephthalate solution.

Step (2) Recovery and Reuse of EG Through Distillation

As shown in the FIGURE, a distillation column with 15 stages in total was prepared for the purification of low-boiling point substances, and discharge pipes for side draw were installed in the 2nd to 8th stages. While the crude bis(2-hydroxyethyl) terephthalate solution prepared in step 1 was continuously fed to the distillation column, purification was carried out. The internal pressure between the bottom and the top of the distillation column was set to 200 to 270 Torr, and the distillation temperature between the bottom and the top of the column was set to 70 to 170° C. First, while the low-boiling substance distilled from the crude bis(2-hydroxyethyl) terephthalate solution was raised from the 1st to the 15th stages of the distillation column, the side draw purging was performed at a fraction of 0.4% by weight in the 2nd to 8th stages (internal temperature: 90 to 150° C.) where the concentration of 2-hydroxyethyl acetate (HA) was the highest among the section where a mixture of monoethylene glycol (MEG) and 2-hydroxyethyl acetate (HA) was present, whereby 2-hydroxyethyl acetate (HA) was prevented from being accumulated in the distillation column. Thereafter, glycols comprising residual ethylene glycol were separated to the top, and the high-boiling point substance comprising bis(2-hydroxyethyl) terephthalate was recovered at the bottom of the distillation column. Recycled ethylene glycol (REG-1) with a 2-hydroxyethyl acetate (HA) content of 0.6% by weight or less was recovered through the above distillation. The recycled ethylene glycol (REG-1) thus recovered was used again in the continuous glycolysis process in step 1 (total number of repeated uses: 10 times).

Step (3) Obtaining Recycled BHET after Further Purification

The high-boiling point substance comprising BHET recovered in step 2 above was subjected to thin film evaporation at 220° C. and 0.08 Torr in a thin film evaporator (VKL70-4S of VTA) to obtain a product from which dimers or higher oligomers had been removed. Thereafter, for adsorption-crystallization, the above product and distilled water were charged to a glass reactor, dissolved at a temperature of 70° C., and then activated carbon was added thereto, followed by stirring for 30 minutes and filtration thereof. The filtrate was cooled to room temperature for the crystallization thereof, filtered, and dried in a vacuum oven, thereby obtaining recycled bis(2-hydroxyethyl) terephthalate.

Example 2

Recycled bis(2-hydroxyethyl) terephthalate was prepared through the same procedure as in steps (1) to (3) of Example 1, except that the side draw purging fraction was adjusted to 0.35% by weight, and the recycled ethylene glycol (REG-2) was recovered and reused in the continuous glycolysis process in step (1) (10 times in total).

Example 3

Recycled bis(2-hydroxyethyl) terephthalate was prepared through the same procedure as in steps (1) to (3) of Example 1, except that the side draw purging fraction was adjusted to 0.28% by weight, and the recycled ethylene glycol (REG-3) was recovered and reused in the continuous glycolysis process in step (1) (10 times in total).

Example 4

Recycled bis(2-hydroxyethyl) terephthalate was prepared through the same procedure as in steps (1) to (3) of Example 1, except that the side draw purging fraction was adjusted to 0.12% by weight, and the recycled ethylene glycol (REG-4) was recovered and reused in the continuous glycolysis process in step (1) (10 times in total).

Example 5

Recycled bis(2-hydroxyethyl) terephthalate was prepared through the same procedure as in steps (1) to (3) of Example 1, except that the side draw purging fraction was adjusted to 0.06% by weight, and the recycled ethylene glycol (REG-5) was recovered and reused in the continuous glycolysis process in step (1) (10 times in total).

Comparative Example 1

Recycled bis(2-hydroxyethyl) terephthalate was prepared through the same procedure as in steps (1) to (3) of Example 1, except that the side draw purging was not performed in step (2), and the recycled ethylene glycol (REG-6) was recovered and reused in the continuous glycolysis process in step (1) (3 times in total).

Comparative Example 2

Recycled bis(2-hydroxyethyl) terephthalate was prepared through the same procedure as in steps (1) to (3) of Example 1, except that the side draw purging was not performed in step (2), and the recycled ethylene glycol (REG-7) was recovered and reused in the continuous glycolysis process in step (1) (7 times in total).

Comparative Example 3

Recycled bis(2-hydroxyethyl) terephthalate was prepared through the same procedure as in steps (1) to (3) of Example 1, except that the side draw purging was not performed in step (2), and the recycled ethylene glycol (REG-8) was recovered and reused in the continuous glycolysis process in step (1) (10 times in total).

Test Example

The recycled ethylene glycol or the recycled bis(2-hydroxyethyl) terephthalate of the Examples and Comparative Examples were each tested as follows.

(1) Composition of the Recycled Ethylene Glycol-Gas Chromatography (GC)

About 0.1 g of each recycled ethylene glycol (REG) was diluted in 10 ml of chloroform, filtered (0.45 μm), and analyzed by gas chromatography (model: Agilent 7890B, column: DB-624 (30 m×0.25 mm×1.4 μm), oven temperature: 60° C. (2 minutes)–10° C./minute–260° C. (5 minutes), injector temp.: 250° C., detector temp.: 250° C., flow: 1.5 ml/minute ($N_2$), split ratio: 1/50). The peak area fraction obtained by gas chromatography (GC) analysis was quantified using the calibration curve of a standard material to obtain each content (% by weight) of monoethylene glycol (MEG), diethylene glycol (DEG), triethylene glycol (TEG), and 2-hydroxyethyl acetate (HA).

(2) Composition of Recycled BHET-HPLC

About 0.01 g of each recycled bis(2-hydroxyethyl) terephthalate before and after purification was diluted in about 20 ml of methanol, which was analyzed by high-performance liquid chromatography (HPLC) (model: Waters e2695, column: C18 (4.6×250 mm), 5 μm, UV detector: 242 nm, injection volume: 10 μl, eluent (gradient) A: $H_2O$+$H_3PO_4$, B: acetonitrile) Thereafter, the peak area fraction (%) of the following components among the total peak area of HPLC was obtained. The composition of the recycled BHET was determined for crude BHET and BHET after purification, respectively.

MHET: monohydroxyethyl terephthalate
BHET: bis(2-hydroxyethyl) terephthalate,
DEG-ester-1:2-hydroxyethyl [2-(2-hydroxyethoxy)ethyl] terephthalate
DEG-ester-2: bis [2-(2-hydroxyethoxy)ethyl]benzene-1, 4-dicarboxylate
DEG-ester-3:1,4-benzenedicarboxylic acid, 1,1'-(1,2-ethanediyl)-4-[2-(hydroxyethoxy)ethyl], 4'-(2-hydroxyethyl) ester
DEG-ester-4:1,4-benzenedicarboxylic acid, 1,1'-(1,2-ethanediyl)-4,4'-bis((2-hydroxyethoxy)ethyl) ester
HA-ester: 2-hydroxyethyl(2-acetoxyethyl) terephthalate
Dimer: BHET dimer
Trimer: BHET trimer
Tetramer: BHET tetramer (3) Yellow Index (YID)

The bis(2-hydroxyethyl) terephthalate obtained after purification was dissolved in dimethylformamide at a concentration of 25% by weight at room temperature, and the yellow index was measured after 30 minutes. Transmission data were obtained with Illuminant D65 using Color Flex EZ of Hunterlab at an observer's angle of 2°. The yellow index (YID) value was calculated using a color analyzer in the software.

(4) Melting Point (m.p.)—Differential Scanning Calorimetry (DSC)

The melting point (m.p.) was measured while heating from 30° C. to 280° C. at a rate of 10° C./minute using a differential scanning calorimeter (DSC, TA Instruments Q20).

(5) Moisture Analysis

The moisture content (% by weight) in the recycled ethylene glycol was measured using a Karl-Fischer moisture analyzer (Metro Toledo, Model: V20).

The configuration of the Examples and Comparative Examples, and the compositions of the recycled ethylene glycol and the recycled BHET analyzed through the Test Examples are summarized in Tables 1 and 2 below.

In contrast, in Comparative Examples 1 to 3 in which side draw purging was not performed during the reduced pressure distillation, 2-hydroxyethyl acetate (HA) continued to accumulate, leading to a high concentration. In particular, in Comparative Example 3, in which ethylene glycol was reused 10 times, it reached 2.4% by weight. As a result, the concentration of 2-hydroxyethyl acetate ester compound (HA-ester) in the final purified bis(2-hydroxyethyl) terephthalate was 1.68% by weight, resulting in poor quality.

The invention claimed is:

1. A process for preparing recycled bis(2-hydroxyethyl) terephthalate, which comprises:

TABLE 1

| | | Ex. 1 REG-1 | Ex. 2 REG-2 | Ex. 3 REG-3 | Ex. 4 REG-4 | Ex. 5 REG-5 | C. Ex. 1 REG-6 | C. Ex. 2 REG-7 | C. Ex. 3 REG-8 |
|---|---|---|---|---|---|---|---|---|---|
| Distillation Condition | No. of reuses | 10 | 10 | 10 | 10 | 10 | 3 | 7 | 10 |
| | Side draw purging fraction (% by weight) | 0.40 | 0.35 | 0.28 | 0.12 | 0.06 | — | — | — |
| REG Composition (% by weight) | MEG | 99.80 | 99.78 | 99.75 | 99.55 | 99.30 | 98.50 | 97.79 | 97.18 |
| | DEG | 0.11 | 0.10 | 0.10 | 0.14 | 0.14 | 0.34 | 0.35 | 0.36 |
| | TEG | 0.02 | 0.01 | 0.01 | 0.02 | 0.01 | 0.02 | 0.02 | 0.02 |
| | HA | 0.04 | 0.08 | 0.10 | 0.24 | 0.51 | 1.10 | 1.80 | 2.40 |
| | Water | 0.03 | 0.03 | 0.04 | 0.05 | 0.04 | 0.04 | 0.05 | 0.05 |

TABLE 2

| | | Ex. 1 | Ex. 2 | Ex. 3 | Ex. 4 | Ex. 5 | C. Ex. 1 | C. Ex. 2 | C. Ex. 3 |
|---|---|---|---|---|---|---|---|---|---|
| Crude BHET composition (%) | REG | REG-1 | REG-2 | REG-3 | REG-4 | REG-5 | REG-6 | REG-7 | REG-8 |
| | MHET | 1.25 | 1.55 | 1.23 | 1.25 | 1.77 | 2.56 | 3.01 | 3.46 |
| | BHET | 87.39 | 87.12 | 87.70 | 86.59 | 86.11 | 83.73 | 83.59 | 81.21 |
| | DEG-ester-1 | 0.68 | 0.65 | 0.59 | 0.75 | 0.74 | 1.15 | 0.83 | 1.12 |
| | DEG-ester-2 | 0.19 | 0.09 | 0.12 | 0.5 | 0.53 | 0.87 | 0.64 | 0.92 |
| | HA-ester | 0.05 | 0.08 | 0.11 | 0.19 | 0.32 | 1.16 | 1.45 | 2.34 |
| | DEG-ester-3 | 0.05 | 0.03 | 0.03 | 0.07 | 0.07 | 0.07 | 0.1 | 0.09 |
| | Dimer | 9.63 | 9.81 | 9.53 | 9.88 | 9.72 | 9.72 | 9.65 | 10.10 |
| | DEG-ester-4 | 0.02 | 0.01 | 0.02 | 0.02 | 0.02 | 0.02 | 0.05 | 0.04 |
| | Trimer | 0.70 | 0.63 | 0.65 | 0.71 | 0.68 | 0.68 | 0.65 | 0.69 |
| | Tetramer | 0.04 | 0.03 | 0.02 | 0.04 | 0.04 | 0.04 | 0.03 | 0.03 |
| Purified BHET composition (%) | MHET | 0.44 | 0.53 | 0.44 | 0.38 | 0.68 | 1.32 | 1.48 | 1.74 |
| | BHET | 98.98 | 98.86 | 99.06 | 99.03 | 98.58 | 96.91 | 96.85 | 95.8 |
| | DEG-ester-1 | 0.35 | 0.13 | 0.15 | 0.27 | 0.30 | 0.44 | 0.37 | 0.44 |
| | DEG-ester-2 | 0.07 | 0.08 | 0.04 | 0.06 | 0.08 | 0.11 | 0.1 | 0.09 |
| | HA-ester | 0.03 | 0.05 | 0.06 | 0.11 | 0.19 | 0.84 | 1.01 | 1.68 |
| | DEG-ester-3 | 0.00 | 0.00 | 0.00 | 0.00 | 0.00 | 0.00 | 0.00 | 0.00 |
| | Dimer | 0.13 | 0.35 | 0.25 | 0.15 | 0.17 | 0.38 | 0.19 | 0.25 |
| | DEG-ester-4 | 0.00 | 0.00 | 0.00 | 0.00 | 0.00 | 0.00 | 0.00 | 0.00 |
| | Trimer | 0.00 | 0.00 | 0.00 | 0.00 | 0.00 | 0.00 | 0.00 | 0.00 |
| | Tetramer | 0.00 | 0.00 | 0.00 | 0.00 | 0.00 | 0.00 | 0.00 | 0.00 |
| Purified BHET | YID | 1.78 | 0.97 | 0.65 | 1.23 | 1.88 | 2.51 | 4.34 | 5.14 |
| | m.p. (° C.) | 112.1 | 112.5 | 112.6 | 112.3 | 112.0 | 106.9 | 106.2 | 105.5 |

As can be seen from Tables 1 and 2 above, 2-hydroxyethyl acetate (HA) was prevented from being accumulated through side draw purging during the reduced pressure distillation in Examples 1 to 5. Thus, the concentration of 2-hydroxyethyl acetate (HA) in ethylene glycol that had been reused 10 times was very low at 0.6% by weight or less. As a result, the concentration of 2-hydroxyethyl acetate ester compound (HA-ester) in the final purified bis(2-hydroxyethyl) terephthalate was less than 0.5% by weight, resulting in good quality.

(a) depolymerizing waste polyester by glycolysis to obtain a crude bis(2-hydroxyethyl) terephthalate solution;

(b) distilling the crude bis(2-hydroxyethyl) terephthalate solution to separate a distillate comprising ethylene glycol;

(c) removing an acetate-based compound from the distillate to recover the ethylene glycol; and (d) reusing the recovered ethylene glycol for the glycolysis, wherein a content of the acetate-based compound in the ethylene glycol recovered in step (d) is 1% by weight or less, wherein the separation of the distillate in step (b) is carried out using a distillation column, and wherein the removal of the acetate-based compound in step (c) is carried out by side draw purging in the distillation column.

2. The process for preparing recycled bis(2-hydroxyethyl) terephthalate of claim 1, wherein the glycolysis in step (a) comprises a reaction of waste polyester and ethylene glycol in the presence of an acetate-based catalyst.

3. The process for preparing recycled bis(2-hydroxyethyl) terephthalate of claim 1, wherein the acetate-based compound comprises 2-hydroxyethyl acetate.

4. The process for preparing recycled bis(2-hydroxyethyl) terephthalate of claim 1, wherein the depolymerization in step (a) is carried out in a continuous process.

5. The process for preparing recycled bis(2-hydroxyethyl) terephthalate of claim 4, wherein the continuous process comprises:

(1) feeding a waste polyester raw material to a co-extruder to obtain a co-extrudate;

(2) feeding the co-extrudate to an agitated shaft reactor and depolymerizing it to obtain a first reactant;

(3) feeding the first reactant to a first continuous reactor and depolymerizing it to obtain a second reactant; and (4) feeding the second reactant to a second continuous reactor and depolymerizing it to obtain a third reactant, wherein ethylene glycol is added to at least one of steps (1) to (4).

6. The process for preparing recycled bis(2-hydroxyethyl) terephthalate of claim 1, wherein the separation of the distillate in step (b) using the distillation column is carried out at a pressure of 0.1 Torr to 300 Torr and a temperature of 70° C. to 170° C.

7. The process for preparing recycled bis(2-hydroxyethyl) terephthalate of claim 1, wherein the side draw purging is performed at a fraction of 0.05% by weight to 1% by weight based on a total weight of the crude bis(2-hydroxyethyl) terephthalate solution.

8. The process for preparing recycled bis(2-hydroxyethyl) terephthalate of claim 1, wherein the recycled bis(2-hydroxyethyl) terephthalate is prepared by further carrying out at least one of thin-film distillation under reduced pressure; and dissolution in water and adsorption-crystallization.

* * * * *